(12) United States Patent
Zienert et al.

(10) Patent No.: US 7,718,447 B2
(45) Date of Patent: May 18, 2010

(54) SYSTEM AND METHOD FOR ESTIMATING THE CRYSTALLINITY OF STACKED METAL LINES IN MICROSTRUCTURES

(75) Inventors: Inka Zienert, Dresden (DE);
Moritz-Andreas Meyer, Dresden (DE);
Hartmut Prinz, Dresden (DE)

(73) Assignee: Advanced Micro Devices, Inc., Austin, TX (US)

( * ) Notice: Subject to any disclaimer, the term of this patent is extended or adjusted under 35 U.S.C. 154(b) by 724 days.

(21) Appl. No.: 11/550,044

(22) Filed: Oct. 17, 2006

(65) Prior Publication Data

US 2007/0201615 A1      Aug. 30, 2007

(30) Foreign Application Priority Data

Feb. 28, 2006      (DE) ................. 10 2006 009 247

(51) Int. Cl.
*G01N 23/20*      (2006.01)
(52) U.S. Cl. .................. 438/16; 438/7; 378/70
(58) Field of Classification Search .......... 378/70, 378/71, 73, 48; 438/7, 14, 16; 257/E21.53
See application file for complete search history.

(56) References Cited

U.S. PATENT DOCUMENTS

| | | | | |
|---|---|---|---|---|
| 4,764,945 A | 8/1988 | Abe | ............................. | 378/50 |
| 5,568,531 A | 10/1996 | Nishihagi et al. | .............. | 378/71 |
| 5,587,590 A | 12/1996 | Matsubara | ................... | 257/48 |
| 5,755,877 A | 5/1998 | Kamakura et al. | ............. | 117/85 |
| 6,062,949 A | 5/2000 | Yashiki et al. | ................. | 451/10 |
| 6,349,128 B1 | 2/2002 | Nelson | ......................... | 378/44 |
| 6,466,642 B1 | 10/2002 | Meloni | ......................... | 378/44 |
| 6,611,576 B1 | 8/2003 | Besser et al. | ................... | 378/48 |
| 6,629,879 B1 | 10/2003 | Kim et al. | ..................... | 451/57 |
| 6,953,755 B2 * | 10/2005 | Meyer et al. | ................. | 250/307 |
| 2001/0043668 A1 | 11/2001 | Hayashi et al. | ............... | 378/89 |
| 2003/0128809 A1 | 7/2003 | Umezawa et al. | ............. | 378/70 |

FOREIGN PATENT DOCUMENTS

WO      WO 2006/010091 A2      1/2006

OTHER PUBLICATIONS

Editors: Bunshah, R.F., "Handbook of Hard Coatings", 2001, William Andrew Publishing/Noyes, p. 117.*
Editors: Buschow, K.H.J.; Cahn, R.W.; Flemings, M.C.; Ilschner, B.; Kramer, E.J.; Mahajan, S.; "Encyclopedia of Materials—Science and Technology, vols. 1-11", 2001, Elsevier, pp. 203-205.*
Nogues, J.; Zakharchenko, I.V.; Rao, K.V.; "Comparative scanning tunneling microscopic and rocking-curve X-ray characterization of metallic thin films", 1998, Thin Solid Films 325, pp. 30-35.*

* cited by examiner

*Primary Examiner*—Matthew C Landau
*Assistant Examiner*—Daren Wolverton
(74) *Attorney, Agent, or Firm*—Williams, Morgan & Amerson, P.C.

(57) ABSTRACT

By performing x-ray analysis of stacked metallization layers on the basis of data reduction, the crystalline structure of individual metallization layers may be determined. Consequently, a relationship between electromigration and crystallinity, as well as a correlation between process parameters and materials and the finally obtained crystalline structures of metal lines, may be estimated in a highly efficient manner compared to measurement techniques based on charged particles.

21 Claims, 4 Drawing Sheets

SYSTEM AND METHOD FOR ESTIMATING THE CRYSTALLINITY OF STACKED METAL LINES IN MICROSTRUCTURES

BACKGROUND OF THE INVENTION

1. Field of the Invention

Generally, the present invention relates to the formation of microstructures, such as advanced integrated circuits, and, more particularly, to the formation and non-destructive examination of conductive structures, such as metal regions, and their characteristics during stress conditions.

2. Description of the Related Art

In the fabrication of modern microstructures, such as integrated circuits, there is a continuous drive to steadily reduce the feature sizes of microstructure elements, thereby enhancing the functionality of these structures. For instance, in modern integrated circuits, minimum feature sizes, such as the channel length of field effect transistors, have reached the deep sub-micron range, thereby increasing performance of these circuits in terms of speed and/or power consumption. As the size of individual circuit elements is reduced with every new circuit generation, thereby improving, for example, the switching speed of the transistor elements, the available floor space for interconnect lines electrically connecting the individual circuit elements is also decreased. Consequently, the dimensions of these inter-connect lines have to be reduced to compensate for a reduced amount of available floor space and for an increased number of circuit elements provided per unit die area. The reduced cross-sectional area of the interconnect lines, possibly in combination with an increase of the static power consumption of extremely scaled transistor elements, may require a plurality of stacked metallization layers in order to meet the requirements in view of a tolerable current density in the metal lines.

Advanced integrated circuits, including transistor elements having a critical dimension of 0.13 µm and even less, may, however, require significantly increased current densities in the individual interconnect lines, despite the provision of a relatively large number of metallization layers, owing to the significant number of circuit elements per unit area. Operating the interconnect lines at elevated current densities, however, may entail a plurality of problems related to stress-induced line degradation, which may finally lead to a premature failure of the integrated circuit. One prominent phenomenon in this respect is the current-induced material transportation in metal lines, also referred to as "electromigration," which may lead to the formation of voids within and hillocks next to the metal line, thereby resulting in reduced performance and reliability or complete failure of the device. For instance, aluminum lines embedded into silicon dioxide and/or silicon nitride are frequently used as metal for metallization layers, wherein, as explained above, advanced integrated circuits having critical dimensions of 0.13 µm or less, may require significantly reduced cross-sectional areas of the metal lines and, thus, increased current densities, which may render aluminum less attractive for the formation of metallization layers.

Consequently, aluminum is increasingly being replaced by copper and alloys thereof that exhibit a significantly lower specific resistivity and exhibit significant electromigration effects at considerably higher current densities compared to aluminum. The introduction of copper into the fabrication of microstructures and integrated circuits comes along with a plurality of severe problems residing in copper's characteristic to readily diffuse in silicon dioxide and a plurality of low-k dielectric materials and to have a moderately low adhesion to the low-k dielectrics. To provide the necessary adhesion and to avoid the undesired diffusion of copper atoms into sensitive device regions, it is, therefore, usually necessary to provide a barrier layer between the copper and the dielectric material in which the copper lines are embedded. Although silicon nitride is a dielectric material that effectively prevents the diffusion of copper atoms, selecting silicon nitride as an interlayer dielectric material is less than desirable, since silicon nitride exhibits a moderately high permittivity, thereby increasing the parasitic capacitances of neighboring copper lines. Hence, a thin conductive barrier layer that also imparts the required mechanical stability to the copper is formed to separate the bulk copper from the surrounding dielectric material and only a thin silicon nitride or silicon carbide or silicon carbonitride layer in the form of a capping layer is frequently used in copper-based metallization layers. Currently, tantalum, titanium, tungsten and their compounds with nitrogen and silicon and the like are preferred candidates for a conductive barrier layer, wherein the barrier layer may comprise two or more sub-layers of different composition so as to meet the requirements in terms of diffusion suppressing and adhesion properties.

Another characteristic of copper significantly distinguishing it from aluminum is the fact that copper may not be readily deposited in larger amounts by chemical and physical vapor deposition techniques, in addition to the fact that copper may not be efficiently patterned by anisotropic dry etch processes, thereby requiring a process strategy that is commonly referred to as the damascene or inlaid technique. In the damascene process, a dielectric layer is first formed which is then patterned to include trenches and vias which are subsequently filled with copper, wherein, as previously noted, prior to filling in the copper, a conductive barrier layer may typically be formed on sidewalls of the trenches and vias. The deposition of the bulk copper material into the trenches and vias is usually accomplished by wet chemical deposition processes, such as electroplating and electroless plating, thereby requiring the reliable filling of vias with an aspect ratio of 5 and more with a diameter of 0.3 µm or even less in combination with trenches having a width ranging from 0.1 µm to several µm. Although electrochemical deposition processes for copper are well established in the field of electronic circuit board fabrication, a substantially void-free filling of high aspect ratio vias is an extremely complex and challenging task, wherein the characteristics of the finally obtained copper metal line significantly depend on process parameters, materials and geometry of the structure of interest. Since the geometry of interconnect structures is determined by the design requirements and may not, therefore, be significantly altered for a given microstructure, it is of great importance to estimate and control the impact of materials, such as conductive and non-conductive barrier layers, of the copper microstructure and their mutual interaction on the characteristics of the interconnect structure so as to insure both high yield and the required product reliability. In particular, it is important to identify and monitor degradation and failure mechanisms in interconnect structures for various configurations so as to maintain device reliability for every new device generation or technology node.

One important aspect of copper-based lines and regions with respect to performance is the crystalline structure of the copper and copper alloys, since the effective resistance of the copper lines may depend significantly on the number, size and orientation of the crystal grains in the metal lines. Consequently, the materials used and also the processes used, such as deposition and post-deposition processes, may have a significant influence on the performance of these lines. Furthermore, any operational conditions may alter the crystalline structure, thereby also contributing to a performance degradation. Other degradation processes, such as stress-induced material transport, for example electromigration, may affect the crystallinity of the metal. Thus, great efforts are made in investigating the effect of metal grains on the overall performance of metallization structures, wherein, however, usually complex and destructive measurement procedures may be required. Consequently, a "direct" observation of process- and material-caused effects as well as operation-driven influences on the crystallinity of metal lines may be time-consuming, in particular, when the performance of a plurality of stacked metallization layers has to be evaluated in its entirety.

Since advanced microstructures, such as fast microprocessors, may require increasingly complex interconnects with dense metal structures at extremely reduced dimensions and many inspection techniques are already pushed to their limits, there exists a need for enhanced or alternative techniques, while avoiding or at least reducing one or more of the above-identified problems.

SUMMARY OF THE INVENTION

The following presents a simplified summary of the invention in order to provide a basic understanding of some aspects of the invention. This summary is not an exhaustive overview of the invention. It is not intended to identify key or critical elements of the invention or to delineate the scope of the invention. Its sole purpose is to present some concepts in a simplified form as a prelude to the more detailed description that is discussed later.

Generally, the present invention relates to a technique for monitoring and/or examining and/or controlling the process of manufacturing highly complex metallization structures, such as copper-based metallization layer stacks of sophisticated integrated circuits, with respect to texture-related characteristics, such as size and/or orientation of metal grains in respective metal regions on the basis of x-ray analysis, wherein one or more metallization layers may be subjected to measurement in the presence of still other metallization layers of the metal stack. Consequently, physical failure analysis and reliability studies of highly complex metallization structures, which are usually performed on the basis of charged particle microscopy, may be performed on the basis of x-ray analysis, thereby substantially avoiding negative impact on the characteristics of the metallization stack caused by the measurement process itself. For example, in highly complex copper-based metallization layer stacks including low-k dielectric materials, conventional metrology processes based on charged particle microscopy, such as SEM (scanning electron microscopy), may result in a significant deformation, thereby possibly yielding non-reliable measurement results and also imposing significant constraints with respect to the measurement strategy, due to the substantial "non-transparency" of upper layers with respect to intermediate metallization layers.

Consequently, according to the present invention, the characteristics of x-rays, i.e., their ability to penetrate a significant length into the metallization stack, is exploited in order to obtain substantially three-dimensional information that may include data with respect to grain size and/or grain orientation of the various metallization layers. Based on this three-dimensional measurement data, a "data reduction" may be performed in order to obtain desired texture information in a substantially two-dimensional fashion in order to enable the estimation of texture-specific characteristics of one or more metallization layers of the metal stack. Consequently, the high penetration capability of the x-rays may be taken advantage of so as to extract crystallographic information, while on the other hand, by appropriate data reduction, non-desired information may be suppressed, thereby providing the potential for obtaining crystallographic information in a "layer-resolved" manner. Moreover, due to the advantages of x-ray analysis with respect to sample preparation, that is, the corresponding metallization layer stack may remain fully operational, examination of stress-induced degradation mechanisms may be readily performed, wherein respective measurement data may be obtained with none or only minor delays, thereby also providing the possibility of studying degradation effects in a highly time-resolved manner and/or using the measurement data as an efficient process control in adjusting the crystalline structure of the metallization layers during the corresponding manufacturing process.

According to one illustrative embodiment of the present invention, a method comprises irradiating a portion of a first stacked metallization structure of a microstructure device with an x-ray beam of specified characteristics, wherein the first stacked metallization structure comprises a plurality of layers and each layer comprises a metal region. The method further comprises obtaining first measurement data of the portion on the basis of the x-ray beam and manipulating the first measurement data to obtain manipulated data relating to a texture of one or more of the metal regions. Furthermore, the method comprises extracting information for at least one of the plurality of stacked layers about the texture on the basis of the manipulated data.

According to another illustrative embodiment of the present invention, a method comprises forming a stacked metallization structure of a microstructure device according to a specified manufacturing sequence, wherein the stacked metallization structure comprises a plurality of metallization layers. The method further comprises obtaining information about a texture of metal regions located in two or more of the plurality of metallization layers on the basis of x-ray analysis and correlating at least one process parameter used in the specified manufacturing sequence with the texture information. Finally, the at least one process parameter is controlled on the basis of the correlation.

According to yet another illustrative embodiment of the present invention, a method comprises providing a metallization structure of a microstructure device, wherein the metallization structure comprises a plurality of stacked metallization layers, each of which comprises a metal region with metal grains. Furthermore, the metallization structure is subjected to predefined stress conditions and a distribution of grain orientations is estimated in at least one of the plurality of stacked metallization layers by x-ray analysis under the predefined stress conditions.

BRIEF DESCRIPTION OF THE DRAWINGS

The invention may be understood by reference to the following description taken in conjunction with the accompanying drawings, in which like reference numerals identify like elements, and in which.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE INVENTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The present invention will now be described with reference to the attached figures. Various structures, systems and devices are schematically depicted in the drawings for purposes of explanation only and so as to not obscure the present invention with details that are well known to those skilled in the art. Nevertheless, the attached drawings are included to describe and explain illustrative examples of the present invention. The words and phrases used herein should be understood and interpreted to have a meaning consistent with the understanding of those words and phrases by those skilled in the relevant art. No special definition of a term or phrase, i.e., a definition that is different from the ordinary and customary meaning as understood by those skilled in the art, is intended to be implied by consistent usage of the term or phrase herein. To the extent that a term or phrase is intended to have a special meaning, i.e., a meaning other than that understood by skilled artisans, such a special definition will be expressly set forth in the specification in a definitional manner that directly and unequivocally provides the special definition for the term or phrase.

Generally, the present invention provides a technique for obtaining information with respect to texture-specific characteristics of a metallization layer, which is one of a plurality of metallization layers in a corresponding metallization structure. The information is obtained on the basis of x-ray measurement data, which may be appropriately manipulated so as to enable the extraction of layer-specific information without requiring a specific sample preparation for removing or otherwise manipulating the structure of lower-lying metallization layers. Consequently, a high degree of authenticity of the extracted information relating to texture-specific characteristics, such as the distribution of grain orientations of metal regions and the like, may be accomplished since the respective metallization structures may be maintained fully operational, while at the same time significantly reducing any negative impact of the measurement procedure itself on the characteristics of the metallization stack. As previously explained, in highly advanced microstructure devices, such as microprocessors, complex ASICs or other integrated circuits, highly conductive metals, such as copper, copper alloys and the like, are processed, possibly in combination with respective conductive and dielectric barrier layers, typically in conjunction with low-k dielectric materials, wherein materials, process techniques and environmental conditions during the operation of the finalized semiconductor devices may significantly affect the performance of the respective metallization structure. For example, stress-induced degradation mechanisms, such as electromigration and the like, although intensively studied, may be highly complex and are typically not yet fully understood, thereby requiring meaningful and relevant information with respect to the mutual influences of materials, processes and operational conditions on the reliability of the metallization structure under consideration. In particular, the crystalline structure of the metal lines in sophisticated integrated circuits, typically comprising copper as the main ingredient, may have an increasingly decisive influence as feature sizes of metal lines are steadily reduced. Thus, the influence of materials, process techniques and operational conditions with respect to the crystallinity of the corresponding metal structures is of great importance for enhancing performance and reliability of presently existing and future semiconductor devices. Since x-ray analysis provides a means for probing deeply into metallization structures without significant negative impact on the metal lines and dielectric materials provided in the respective metallization layer, the texture-specific characteristics thereof may be examined under a variety of conditions, wherein the "data reduction" of the present invention enables the extraction of information for a specific metallization level even if a plurality of further metallization layers are present. Hence, valuable information with respect to grain distribution, grain size and the like may be obtained in a reliable yet fast and efficient manner.

It should be noted that the present invention is particularly advantageous in the context of copper-based interconnect structures since these structures will preferably be used in advanced microstructures, such as fast and powerful microprocessors, wherein especially the problem of electromigration may significantly impact further developments in fabricating sophisticated integrated circuits. The principles of the present invention may, however, be readily applied to any microstructure of interest, in which stress-induced mass transport phenomena may significantly influence the operation and the reliability of the microstructure. Consequently, stress-induced migration problems and their influence on texture-related characteristics of materials may be effectively investigated for any type of interesting conductive material, such as metals, metal alloys or metal compounds used in present and future microstructure systems. The present invention should therefore not be considered as being restricted to copper-based interconnect structures unless such restrictions are explicitly set forth in specific embodiments as presented in the following description as well as in the appended claims.

As is well known, the degradation of inlaid, i.e., embedded, metal lines is related to directed mass transport within the line. The gradient of the electrical potential gives migrating atoms a preferred direction to the anode. Local temperature peaks caused by increased electrical current densities lead to temperature gradients during operation of a microstructure device and therefore also thermal migration is closely connected with electromigration. Furthermore, mechanical stress gradients may also have a significant influence on the characteristics of metal lines and thus on their crystallinity. Since the size and orientation of grains within the metal lines may significantly determine their characteristics with respect to performance and reliability, the process techniques for forming the metal lines as well as the materials involved may have to be thoroughly monitored and controlled in order to maintain device reliability and performance. Consequently, the present invention provides, in some aspects, the potential of a sensitive process control or monitoring based on statistically relevant information and for the study of texture-specific alteration mechanisms for highly authentic samples enhancing the understanding of many aspects of the interconnect technology and reduced reliability related failures in interconnect structures. To this end, fully embedded and operational interconnect structures, or any intermediate forms thereof, including a plurality of metallization levels may be subjected to specified stress conditions while monitoring texture-specific characteristics of the interconnect structure in a spatially highly resolved fashion, that is, providing information of the distribution of grain orientations in a "layer resolved" manner. Since the analysis is based on x-ray technology, low impact on the operational behavior of the sample as well as rapid data gathering may be accomplished, thereby providing the potential for effectively visualizing even subtle changes of the grain structure of metal interconnect structures during operation. Moreover, these characteristics of the measurement technique of the present invention also provide the possibility of obtaining valuable information on the "quality" of the respective manufacturing sequence for fabricating a specific type of metallization structure, which therefore may enable an efficient process control, since information obtained on the crystallinity of the respective metal level may even be provided in the form of "inline" measurement data.

Figure 1A:
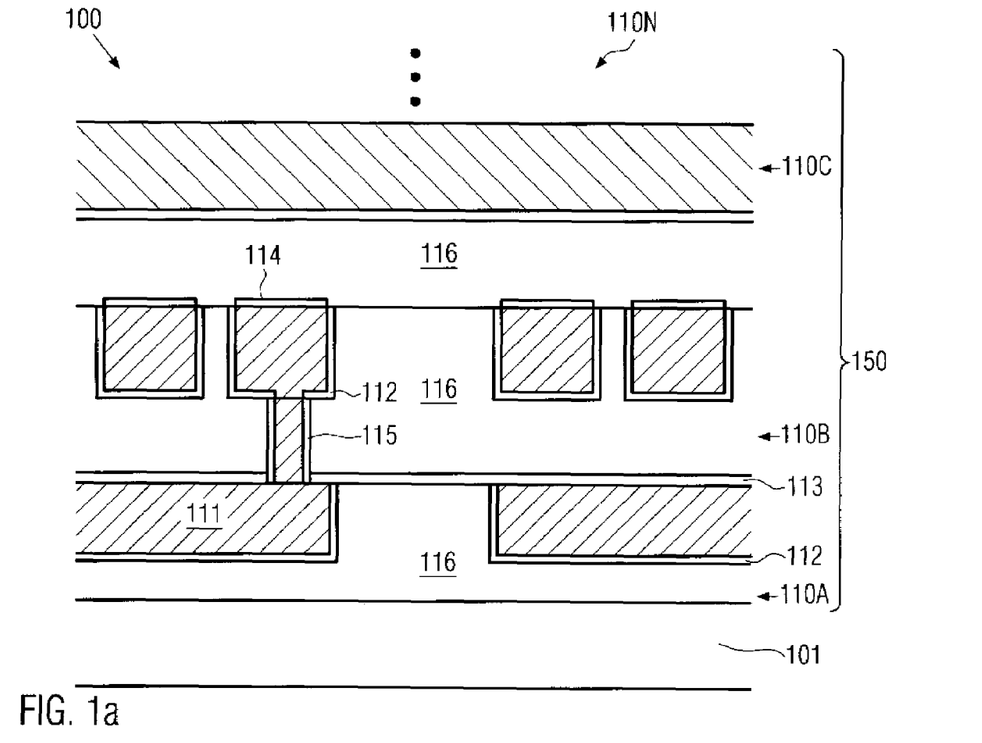
FIG. 1a schematically illustrates a cross-sectional view of a metallization structure, such as a stack of copper-based metallization layers of an integrated circuit that may be subjected to a texture-related x-ray analysis according to the present invention.

With reference to FIGS. 1a-1f, 2 and 3, further illustrative embodiments of the present invention will now be described in more detail. FIG. 1a schematically illustrates a cross-sectional view of a microstructure device 100, which in some illustrative embodiments may represent a test structure used for the formation of sophisticated integrated circuits or may represent a portion of an actual semiconductor device. The microstructure device 100 may comprise a substrate 101, such as a semiconductor substrate or any other appropriate carrier for forming therein and thereon respective circuit elements of an integrated circuit. In other cases, the substrate 101 may act as a carrier for a stacked metallization structure 150 formed thereon. The stacked metallization structure 150 may comprise a plurality of individual metallization layers 110A, 110B, 110C, 110N, wherein the number N of metallization layers 110 may depend on device and process requirements. For example, the number of metallization layers 110A, 110B, 110C, 110N may range from 2-10 or more, wherein, for instance, for highly complex copper-based microprocessors, approximately 5-10 metallization layers 110A, 110B, 110C, 110N may typically be provided.

Each of the metallization layers 110A, 110B, 110C, 110N may include one or more metal regions 111 which may, in illustrative embodiments, comprise copper or copper alloys, or any other highly conductive materials. For example, typically in copper-based metallization structures, the metal regions 111 may be confined by conductive and/or dielectric barrier layers, wherein conductive barrier layers may comprise well-approved materials, such as tantalum, tantalum nitride, titanium, titanium nitride, tungsten, tungsten nitride, cobalt/tungsten/phosphorous compounds, cobalt/tungsten/boron compounds and the like. For example, a conductive barrier layer 112 and a dielectric capping layer 113, for instance comprised of silicon carbide, silicon nitride, nitrogen-enriched silicon carbide, or any combinations thereof, may be provided for the metal regions 111 in the first metallization layer 110A. As a further example, a conductive capping layer 114 in combination with the conductive barrier layer 112 may be provided for the metal regions 111 of the second metallization layer 110B in order to demonstrate various design possibilities for the stacked metallization structure 150. Furthermore, the metal regions 111 in the various metallization layers 110A, 110B, 110C, 110N may have any geometric configuration as prescribed by design rules wherein, however, the essential portion of the metal material in the various regions 111 may be provided in the form of metal lines and metal plates, while only a minor portion of the metal material may be contained in respective vias 115.

Furthermore, each of the metallization layers 110A, 110B, 110C, 110N may comprise a dielectric layer 116, in which the metal regions 111 are embedded, wherein, depending on device requirements, the dielectric layers 116 may have a differing configuration and may comprise well-approved dielectric materials, such as silicon dioxide, silicon nitride, silicon oxynitride, silicon carbide and the like, possibly in combination with low-k dielectric materials, which may have a relative permittivity of 3.0 and significantly less. It should be appreciated that although the microstructure device 100 may represent a specific test structure fabricated on dedicated test wafers or on product wafers at specific locations, such as scribe lines and the like, the configuration of the metallization layer stack 150 may have a high degree of similarity to a corresponding metallization structure of actual product devices in order to provide high authenticity of measurement data gathered on the basis of the structure 100 as shown in FIG. 1a. That is, although the various metallization layers 110A, 110B, 110C, 110N may be designed so as to enable, in some illustrative embodiments, the operation of the structure 150 according to a specified test regime, nevertheless the corresponding components of each metallization layer may be formed in accordance with design rules of actual devices. In other illustrative embodiments, when the electrical functionality of the structure 150 may not be required for obtaining the desired information, the design of the metallization structure 150 may be identical to that of actual product devices.

A typical process flow for forming the microstructure device 100 as shown in FIG. 1a may comprise the following processes, wherein, for convenience, the fabrication of only one metallization layer, for instance the layer 110A, will be described in more detail. Thus, after forming any circuit elements or other microstructural features in and on the substrate 101, when the substrate 101 is to represent a product substrate in which the device 100 is to be fabricated, the dielectric layer 116 may be formed on the basis of any appropriate technique. For instance, the dielectric layer 116 may comprise a dielectric etch stop layer (not shown) which may be used during the patterning of the dielectric material for forming any vias, such as the via 115 in the second metallization layer 110B, wherein well-established deposition techniques such as plasma enhanced chemical vapor deposition (PECVD) and the like may be used. Thereafter, the layer 116 may be formed in one or more manufacturing steps, depending on the configuration of the layer 116, wherein the fabrication of the metal regions 111 may be performed after patterning of the dielectric layer 116 or prior to forming the layer 116, when the metal regions 111 are first formed in a sacrificial material, which may be removed after the formation of the metal regions 111. In any case, any appropriate material may be used, such as polymer materials, porous silicon-based dielectric materials and the like.

The conductive barrier layer 112, if provided, may be formed by any appropriate manufacturing technique, such as physical vapor deposition (PVD), sputter deposition, chemical vapor deposition (CVD), atomic layer deposition (ALD), electrochemical deposition and the like. Thereafter, the highly conductive metal may be deposited on the basis of any appropriate technique, wherein, for copper-based metallization structures, typically electrochemical deposition techniques, such as electroplating, electroless plating and the like, may be used.

During the formation of the metal regions, the corresponding process technique may have a significant influence on the finally obtained crystallinity of the metal within the regions 111 with respect to a grain size and/or grain orientation. For example, frequently a so-called seed layer may be used prior to the deposition of the bulk material by electroplating, wherein the characteristics of the seed layer may significantly affect the crystalline structure of the resulting metal. As an example, CVD-deposited copper may, despite its advantageous behavior with respect to step coverage, result in a copper that is inferior with respect to its crystallinity compared to a sputter-deposited seed layer. Moreover, the electrochemical deposition process itself as well as any post-deposition processes may also affect the finally obtained crystallinity. For instance, after the deposition of the corresponding metal, such as copper, typically excess material is formed on the dielectric layer 116, which has to be removed afterwards on the basis of electrochemical etch techniques and/or chemical mechanical polishing (CMP), which may apply a high mechanical stress to the resulting metal regions especially for low-k dielectric materials within the layer 116, as these low-k dielectric layers typically exhibit a significantly lower mechanical stability. Thus, after deposition and possibly after CMP, appropriate anneal processes may be performed in order to improve the crystalline structure of the resulting metal regions 111.

Figure 1B:
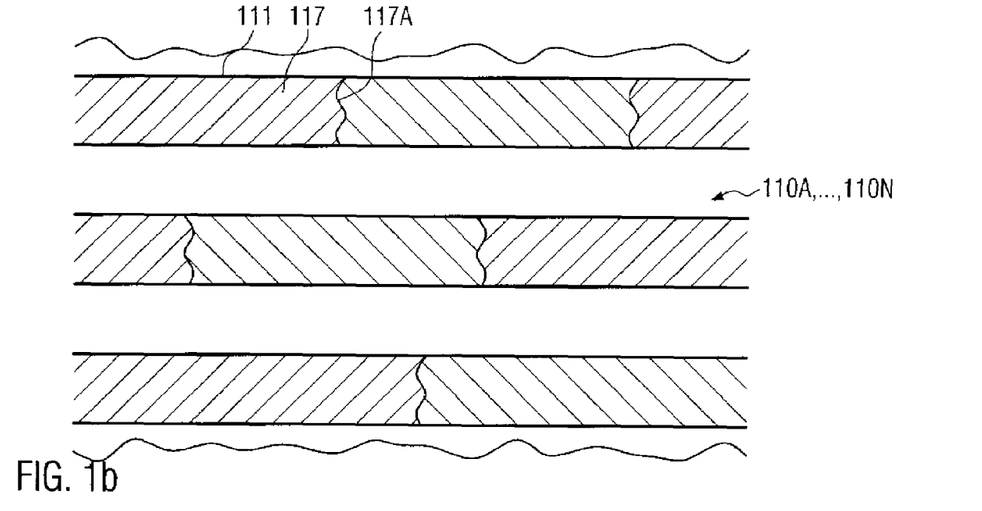
FIG. 1b schematically illustrates a top view of a metallization layer including metal regions, the grain size and/or orientation of which may be estimated on the basis of an analysis technique according to illustrative embodiments of the present invention.

FIG. 1b schematically illustrates a top view of the device 100, wherein a plurality of metal regions 111, for instance in the form of metal lines, may be provided. After the above-described process sequence, the metal lines 111 may have a specific texture, that is, the metal in the lines 111 may comprise a plurality of metal grains 117, which may represent a more or less crystalline area. Typically, a width of the metal line 111 may be significantly less than 1 μm, at least in lower-lying metallization layers such as layers 111A, 111B in sophisticated semiconductor devices, while a length of the metal line 111 may extend along several tenths of micrometers. Frequently, in view of electrical performance, it may be desirable to provide a reduced number of grains 117 within a single metal line 111 in order to reduce scattering events for the charge carriers at grain boundaries 117A. Consequently, during the manufacturing of the various metallization layers 110A . . . 110N, process techniques may be used in order to reduce the number of grain boundaries 117A, that is, to increase the size of the individual grains 117 in each metal line 111. Moreover, the performance of the metal line 111 may also depend on the crystalline orientation of the respective grains 117, since different crystallographic orientation with respect to the length direction or perpendicularly thereto may also significantly influence the characteristics with respect to charge carrier transport and/or stress-induced degradation effects, such as electromigration. For instance, for copper-based metallization layers, the lines 111 having copper grains 117 with a crystallographic orientation (111) perpendicular to the drawing plane of FIG. 1b may exhibit a higher resistance to electromigration than other orientations of copper crystals. Consequently, it is important to monitor the characteristics of the metal grains 117 during the complex process of manufacturing the same and/or during the operation of the device 100, wherein an influence of the measuring strategy on the obtained information should be maintained at a low level in order to provide a high degree of authenticity, thereby rendering conventional techniques based on charged particles less efficient, due to the low penetration depth requiring sophisticated sample preparation techniques which, in combination with the physical interaction of the charged particles, may significantly affect the overall configuration of the sample.

Figure 1C:
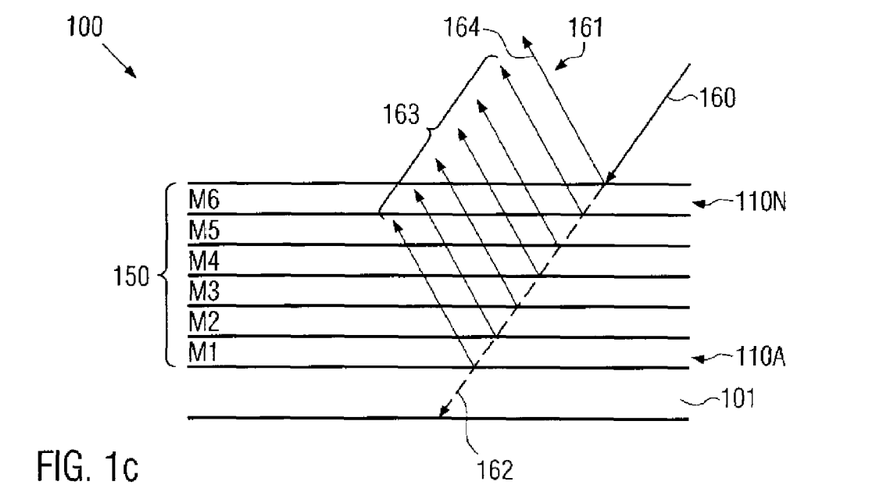
FIG. 1c illustrates a schematic cross-sectional view of a multi-layer metallization stack during the incidence of an x-ray beam for analysis of texture-related characteristics of one or more metallization layers according to illustrative embodiments of the present invention.

FIG. 1c schematically illustrates the microstructure device 100, in which the metallization structure 150 may comprise, for example, six metallization layers, also indicated as M1, M2, M3, M4, M5, M6 which may correspond to the layers 110A . . . 110N as illustrated and explained with reference to FIGS. 1a and 1b. For example, the metallization structure 150 may be formed in accordance with design rules corresponding to those of respective metallization layers of copper-based integrated circuits and the like. Consequently, in some illustrative embodiments, the metallization layers M1, M2 M3, M4, M5, M6 may have experienced the same manufacturing sequences, metrology processes and the like as any devices on product substrates, or the microstructure device 100 may also be provided on a product substrate at dedicated test positions, while in other embodiments the structure 100 may represent an actual product device used for test purposes. For a probing beam, the metallization structure 150 may represent a three-dimensional structure containing a plurality of metal regions corresponding to the metal regions 111 and to a certain degree to the vias 115, and dielectric material comprised in the various dielectric layers 116 and any dielectric capping layers such as the layer 113. Consequently, an x-ray beam 160, impinging on the device 100, may undergo interaction with the material contained in the structure 150, wherein the type of interaction significantly depends on the characteristics of the various materials, as well as on the characteristics of the incident x-ray beam 160. For example, for moderately high beam energies of several keV as are typically required for performing a crystallographic analysis of materials, a penetration depth of the beam 160 may be greater than or comparable to the thickness of the metallization structure 150, thereby providing a plurality of reflected or scattered and transmitted beams 161, 162 which may have interacted with the metallization structure 150 at varying thicknesses. For example, the uppermost metallization layer M6 or 110N may be "seen" by the incoming x-ray beam 160 as a material surface comprising a metal having formed therein a plurality of metal grains, such as the grains 117, having a specific size and orientation. Consequently, a fraction of the incident beam 160 may interact with the crystallographic structure in the grains 117, thereby producing a reflected or scattered beam for a specified angle of incidence for a specified beam energy, i.e., wavelength, when a specified entirety of crystalline planes meets the Bragg condition. Similarly, due to restricted thickness of the uppermost metallization layer 110N, most of the incident beam 160 may further proceed into the structure 150, thereby encountering further metal grains, which may also interact with the incident beam in order to produce reflected and scattered beam components. It should be appreciated that other material components, such as the dielectric materials, may interact with the incoming beam, thereby also producing secondary radiation which may be included in the beams 161 and 162. Consequently, the entirety of beams 161, 162, which may be detected by appropriate detection means, such as semiconductor detectors and the like, may include information regarding the entirety of the stack 150, which may also include information of the response of the individual layers 110A . . . 110N to the incident beam 160 or the respective portions thereof after interaction within the structure 150. In order to obtain information on the texture-specific characteristics of the metallization structure 150 in a more spatially localized manner, "three-dimensional" information reflecting the response of a certain volume of the structure 150 and contained in the beams 161, 162 may be "reduced" so as to obtain substantially "two-dimensional" information, which may represent information on a substantially horizontal "slice" of the structure 150. For instance, the plurality of beams 161 may be detected and may be analyzed by any appropriate analysis technique for obtaining structural information with respect to the size and/or orientation of the grains 117, wherein measurement data and/or a manipulated version thereof may be related to appropriate "reference" data in order to estimate the magnitude of the effect, which may be provided, for instance, by the uppermost metallization layer 110N compared to the rest of the layers 110A, 110B, 110C, 110N. Consequently, as indicated in FIG. 1c, the measurement data represented by the beams 161 may be manipulated so as to "extract" information related to a portion 164 that substantially corresponds to the uppermost metallization layer 110N on the basis of appropriate reference data representing the combined information corresponding to the scattered or reflected beams 163, although these beams are actually not separated.

Consequently, the three-dimensional information included in the plurality of scattered beams 161 may be reduced to the "two-dimensional" information corresponding to the beam component 164. It should be appreciated that the scattered beam 161 is actually a single beam or a portion thereof which may be detected by a corresponding detector element and the above process of data reduction does not provide real "separated" beams, as is illustratively depicted in FIG. 1c. Rather, the data reduction should be understood as a data manipulation, in which a wanted signal is extracted from a "noisy" underground, i.e., the information produced by the lower-lying layers, in order to obtain the information contained in the portion of the detected beam that substantially contains the information originating from the interaction with the layer 110N, wherein the corresponding "beam" 164 illustrated in the figures may, however, not be physically separated from the remaining beam components 163 stemming from an interaction with the remaining metallization layers. For example, in some illustrative embodiments, the incident x-ray beam 160 may be provided as a substantially mono-energetic beam having an energy of several keV, wherein an angle of incidence may be varied and the resulting scattered or transmitted beams 161 may be detected and recorded. Based on the resulting intensity variation with respect to the angle of incidence, in combination with the provision of appropriate reference data, which may represent unwanted signal portions stemming from the metallization layers 110A, 110B, 110C, 110N, information about the orientation and/or size of the grains of the metallization layer 110N may be extracted. In other illustrative embodiments, the beam 160 may comprise a plurality of different wavelength components and an angle of detection for the scattered beams 161 may be varied in order to obtain a corresponding intensity variation for extracting information on the crystallinity of metallization layer 110N.

Appropriate reference data may, in some embodiments, be established on the basis of reference measurements, possibly in combination with respective simulation calculations, as respective electromagnetic interactions in a wide variety of materials is well understood and corresponding calculations may be performed with high accuracy, depending on the available computational resources. For instance, simulation calculations may be performed in advance for a variety of device configurations for each of the metallization layers 110A, 110B, 110C, 110N on the basis of appropriate material models, especially for the metal grains 117, in order to obtain a plurality of quantitative intensity distributions of the simulated "scattered beams." For example, for a substantially ideal metallization structure 150, it may be assumed that, in each metallization layer, a high uniformity in grain size and grain orientation may be obtained during manufacturing and may still be maintained during the formation of any subsequent metallization layers, which may be assumed to also have respective grain sizes and orientations. With a correspondingly assumed configuration, the resulting intensity distribution with a varying angle of incidence for a given beam energy may be calculated. Similarly, for one or more of the layers 110A, 110B, 110C, 110N, a different configuration may be assumed, for instance by altering the (virtual) distribution of grain orientations in the respective metal lines and the like, and a corresponding simulation result may be recorded as a further set of reference data. Based on a plurality of respective different sets of reference data, an appropriate process of data reduction for actual measurement data obtained from the beam 161 may be performed to estimate the texture of one or more of the layers 110A, 110B, 110C, 110N, wherein the reference data may be stored in a library in order to enhance data procession speed when comparing the measurement data with the reference data. Additionally or alternatively, the process of data reduction may be based on reference measurements, as will be described with reference to FIGS. 1d and 1f for further illustrative embodiments of the present invention.

Figure 1D:
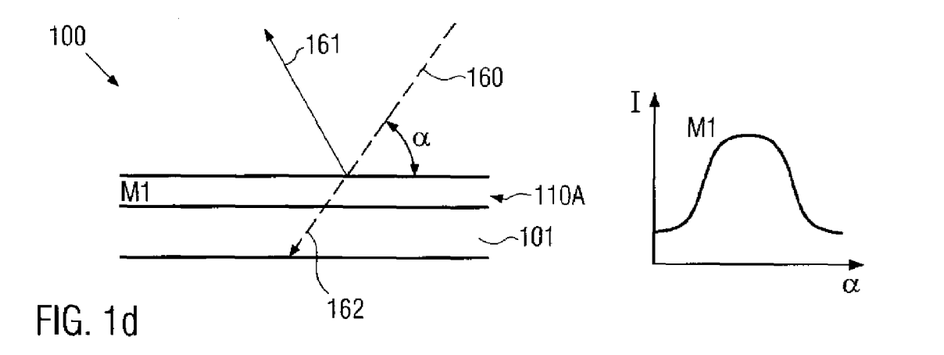
FIG. 1d schematically illustrates a cross-sectional view of a microstructure device including one metallization layer for obtaining measurement data relating to texture-related characteristics according to an illustrative embodiment.

FIG. 1d schematically illustrates a cross-sectional view of the microstructure device 100 in an early manufacturing stage, wherein it should be appreciated that the structure 100 may not actually represent the identical structure as shown, for instance, in FIG. 1c after the formation of six metallization layers, but may represent an equivalent structure having formed thereon the first metallization layer 110A. In this manufacturing stage, the x-ray beam 160 may be provided as a substantially mono-energetic beam, wherein the angle of incidence, indicated as α, may be varied within an appropriate range of values, for instance for enabling the identification of one or more crystallographic orientations of interest within the metal regions in the layer 110A. The resulting scattered or reflected beam 161 may be detected by any appropriate detector in order to obtain the corresponding intensity of the beam 161 with a variation of the angle of incidence α. For example, at the right side of FIG. 1d, a corresponding diagram may illustratively represent an intensity distribution for the beam 161 over a certain range of angles of incidence α. It should be appreciated that the diagram of FIG. 1d is only of illustrative nature wherein, for instance, actual measurement data may be appropriately manipulated on the basis of well-established techniques, such as data smoothing, data fitting and the like. Moreover, respective measurement data, indicated as M1, as represented by the diagram of FIG. 1d may, in some cases, be obtained on the basis of a moderately high number of samples processed on the basis of substantially identical process conditions in order to enhance the statistical relevance of the respective measurement data. In still other illustrative embodiments, the measurement data obtained according to FIG. 1d may also be correlated to measurement data obtained by other measurement techniques, such as electron microscopy, in order to obtain a quantitative measure or additional information that enables the categorization of the x-ray measurement data, when combining measurement data of different samples.

Figure 1E:
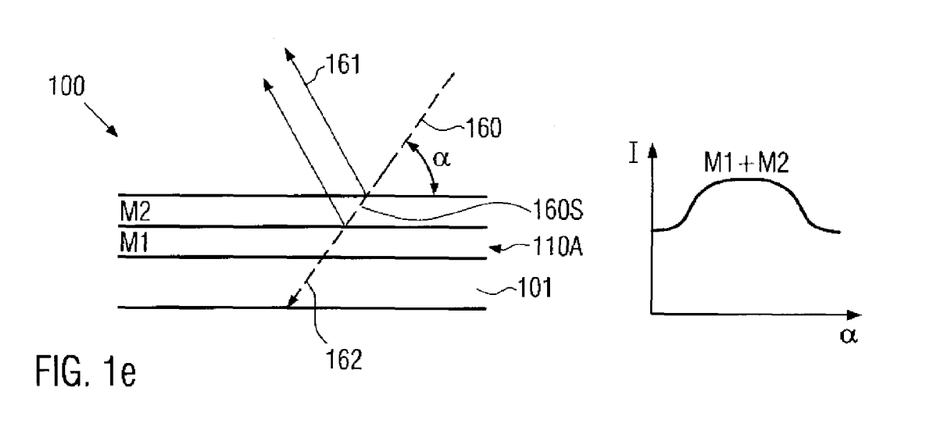
FIG. 1e schematically illustrates a cross-sectional view of the microstructure device including two stacked metallization layers for obtaining a further measurement data that may be used in combination with the previously obtained measurement data according to illustrative embodiments.

FIG. 1e schematically illustrates the microstructure device 100 in a further advanced manufacturing stage, in which a further metallization layer 110B is formed on the first metallization layer 110A, wherein it should also be appreciated that the device 100 may not necessarily represent the same device 100 as shown in FIG. 1d, but may represent an equivalent device in which the first metallization layer 110A is substantially equivalent to the layer 110A of FIG. 1d. Similarly as described above, a portion of the device 100 may be irradiated with the x-ray beam 160 of specified characteristics and the resulting scattered or reflected beam 161 may be detected. The corresponding measurement data may be represented by a corresponding diagram as shown at the right side of FIG. 1e, wherein the resulting intensity distribution now represents the combined response of the layers 110A and 110B to the incident beam 160. Thus, the corresponding measurement result may include the desired information with respect to the metallization layer 110B, which however is "obscured" by the information produced by the first metallization layer 110A (and of course by the substrate 101). Consequently, in some illustrative embodiments, the previous measurement data or any manipulated version thereof may be used as reference data, which may be related or, in illustrative embodiments, "subtracted" in any appropriate form in order to produce respective measurement data substantially corresponding to the response of the metallization layer 110B.

Figure 1F:
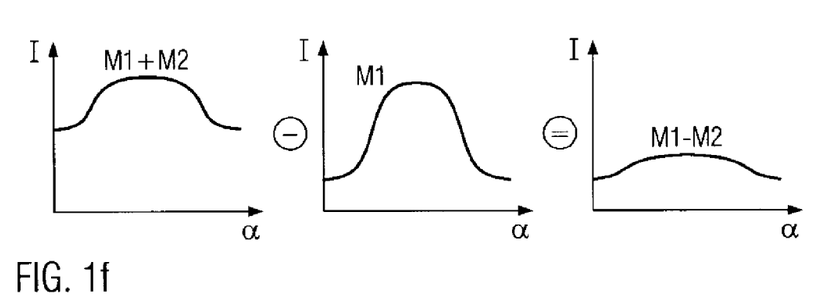
FIG. 1f schematically illustrates a data manipulation process in a simplified form for obtaining manipulated data including information on the texture characteristics of a single layer of the stack of FIG. 1e according to one illustrative embodiment of the present invention.

FIG. 1f schematically illustrates a corresponding simplified data manipulation sequence for obtaining an appropriate measurement data set for estimating the texture-specific characteristics of the metallization layer 110B. For instance, the reference data or measurement data M1 obtained during the first measurement according to FIG. 1d may be "subtracted" from the second measurement data M1+M2 obtained during the measurement according to FIG. 1e in order to obtain differential data M2 as indicated by the right side of the "equation" illustrated in FIG. 1f. It should be appreciated that the "subtraction" operation as indicated in FIG. 1f may include any appropriate data manipulation process for producing the differential data M2. For instance, as previously indicated, the raw data may be subjected to data smoothing, fitting, peak detection and the like prior to performing the data reduction according to FIG. 1f. Moreover, again referring to FIGS. 1d and 1e, it may be appreciated that the situation for the first metallization layer 110A in FIG. 1e is different compared to the metallization layer 110A of FIG. 1d, even though the incident beam 160 may be identical in both cases. That is, while according to FIG. 1d the completely "undisturbed" beam 160 penetrates the metallization layer 110A, according to FIG. 1e a modified version, indicated as 160S, of the beam 160 may impinge on the first metallization layer 110A, since the beam 160 has already undergone significant interaction with the second metallization layer 110B. Consequently, at least the intensity of the beams 160S and 160 incident on the first metallization layers 110A of FIGS. 1d and 1e is different and also the divergence of the beam 160S may be increased compared to that of the beam 160. Consequently, in some illustrative embodiments, the corresponding effect caused by the difference in the incoming beams 160 and 160S may be taken into consideration prior to the data reduction corresponding to FIG. 1f in that the respective reference data M1 may be "corrected" by an appropriate correction factor or correction function. For instance, a reduced height of the intensity distribution of the reference data M1, possibly in combination with a broader distribution around corresponding peaks, may be used for the corresponding data reduction according to FIG. 1f in order to take into consideration the reduced intensity and the increased divergence of the beam 160S.

Moreover, as previously explained, the measurement data M1 and M1+M2 or M1−M2 may be compared with respective simulation calculations in order to more clearly identify respective crystallographic characteristics and/or to enhance the authenticity of the respective simulations. Furthermore, the second measurement data M1+M2 obtained according to, for instance, a measurement process as shown inure FIG. 1e may also be used as respective reference data for measuring a subsequent metallization layer, that is, the third metallization layer 110C, according to the same principles as outlined with reference to FIGS. 1d-1f. Thus, the metallization structure 150 as shown in FIG. 1c may be measured with respect to the texture characteristics of the uppermost layer 110N on the basis of respective reference data obtained for the layers 110A, 110B, 110C, 110N, similarly as is described above. Depending on the amount of available reference data, respective "layer resolved" texture-specific information may also be extracted for intermediate metallization layers by correspondingly correcting for the influence of overlaying and underlying layers. It should be appreciated that, due to the low impact of the x-ray beam 160 on the characteristics of the metallization structure 150 in combination with the high penetration depth and the moderately low effort for sample preparation, corresponding measurement data may be readily gathered on fully embedded and operational structures, thereby rendering the measurement technique based on x-ray analysis with a respective data reduction highly advantageous for identifying failure mechanisms and for identifying relevant process parameters of a respective manufacturing process.

Figure 2:
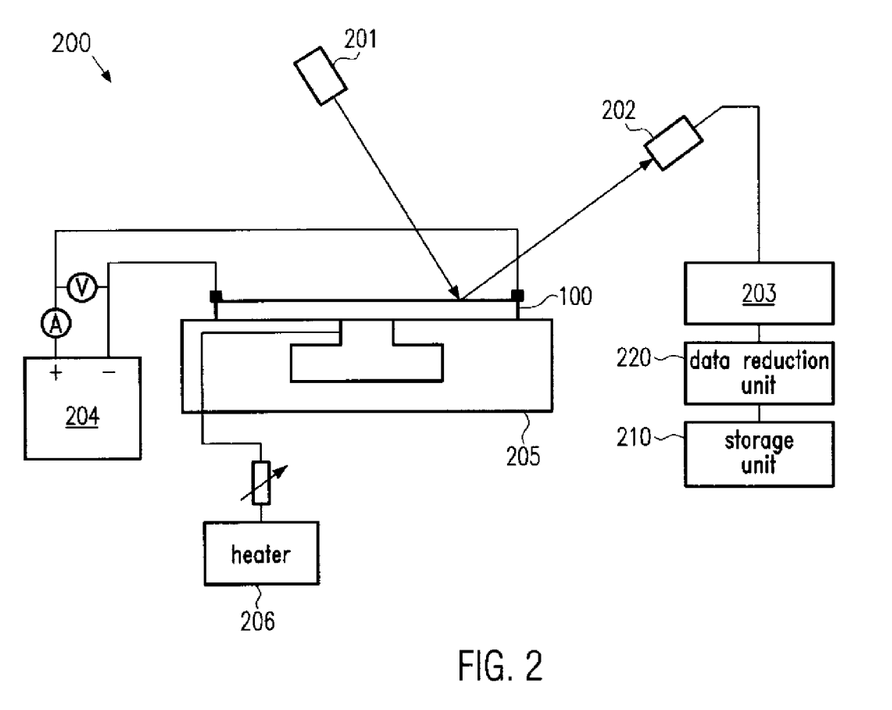
FIG. 2 schematically illustrates a system for estimating texture-specific characteristics of a metallization stack under specified stress conditions according to illustrative embodiments of the present invention.

With reference to FIG. 2, further illustrative embodiments of the present invention will now be described in more detail, in which the monitoring and investigation of texture characteristics during specified stress conditions may be performed on the basis of the above-described measurement techniques.

In FIG. 2, a system 200 comprises an x-ray source 201 and an x-ray detector 202 that is configured to detect scattered or reflected radiation generated by the incoming x-ray beam, as is previously described with reference to the x-ray beam 160 and the corresponding scattered or reflected beams 161 and 162. Moreover, the detector 202 is configured to provide respective measurement data, such as intensity values, wherein the radiation source 201 and the detector 202 may be configured to operate with varying angles of incidence. Furthermore, the detector 202 is connected to a signal processing unit 203 configured to obtain respective measurement data and manipulate and/or store the respective data. The system 200 further comprises a sample holder 205 configured to receive and hold in position an appropriate sample, such as the microstructure device 100 as described with reference to FIGS. 1a-1e. The sample holder 205 may represent any appropriate process chamber for applying specified stress conditions, which may for instance comprise respective environmental conditions, such as temperature, humidity, pressure and the like. For example, the system 200 may comprise an adjustable current source 204 that may be connected to the microstructure device by appropriate contact pads (not shown). Moreover, the system 200 may comprise a heater 206 configured to adjustably provide heat to the sample holder 205 in order to adjust the temperature of the respective sample. Furthermore, the system 200 may comprise a storage unit 210 for receiving corresponding data from the signal processing unit 203, for instance in the form of intensity distributions as are illustratively shown in FIGS. 1e-1f, or in any other form that indicates a characteristic of the grain size and/or orientation, wherein a part of the respective data may be used as reference data, as is previously described. Moreover, respective data of simulation calculations may also be stored in the unit 210 or may be generated on demand within the unit 210 by means of appropriate computer means. Furthermore, the system 200 may comprise a data reduction unit 220 configured to operate on respective data sets stored in the storage unit 210 so as to obtain relevant reduced or differential data, from which respective information on texture-specific characteristics may be extracted. For instance, the unit 220 may be configured to automatically estimate the distribution of grain orientations on the basis of respective differential data, such as a data M1–M2 as shown in FIG. 1f, by, for instance, identifying a width and/or a position of a respective peak or maximum of the intensity distribution, and/or by comparing the respective differential data with appropriate reference data for a variety of configurations for respective metal grains.

During the operation of the system 200, an appropriate sample, such as the device 100, may be mounted on the sample holder 205 and specified stress conditions may be applied. Since the investigation of electromigration is of great interest for the development of interconnect structures of highly complex integrated circuits, preferably the stress condition includes the application of a specified current by means of the adjustable current source 204 to create a specific initial current density in one or more layers of interest, such as the upper-most metallization layer, as is for instance shown in FIG. 1c. Furthermore, the sample holder 205 may be heated to a specified temperature, or a specific temperature distribution may be generated in order to induce a specific temperature gradient within the respective measurement sample.

During the application of the specified stress conditions, the x-ray beam may be directed to the sample, either continuously or intermittently at predefined time intervals, and the corresponding scattered or reflected radiation is received by the detector 202. For instance, the sample may be provided in the form of a lamella and the transmitted or scattered or reflected x-ray beam may be detected and processed to provide the respective differential or reduced data that enables the estimation of the corresponding texture-specific characteristics. Depending on the computational resources and amount of data manipulation and process simulation, respective information on the texture characteristics may be obtained in a substantially real-time fashion and may be made visible in a substantially time-related fashion with respect to the process conditions, while, in still other embodiments, the corresponding measurement data may be stored and may be analyzed at any later stage. Consequently, a correlation between stress-induced degradation mechanisms and texture characteristics may be efficiently established to detect relevant degradation mechanisms. Since sample preparation is significantly less complex compared to the preparation of samples for electron microscopy, respective data may be readily obtained within a reasonable time period, thereby also enabling an effective process control for the fabrication of complex metallization structures.

Figure 3:
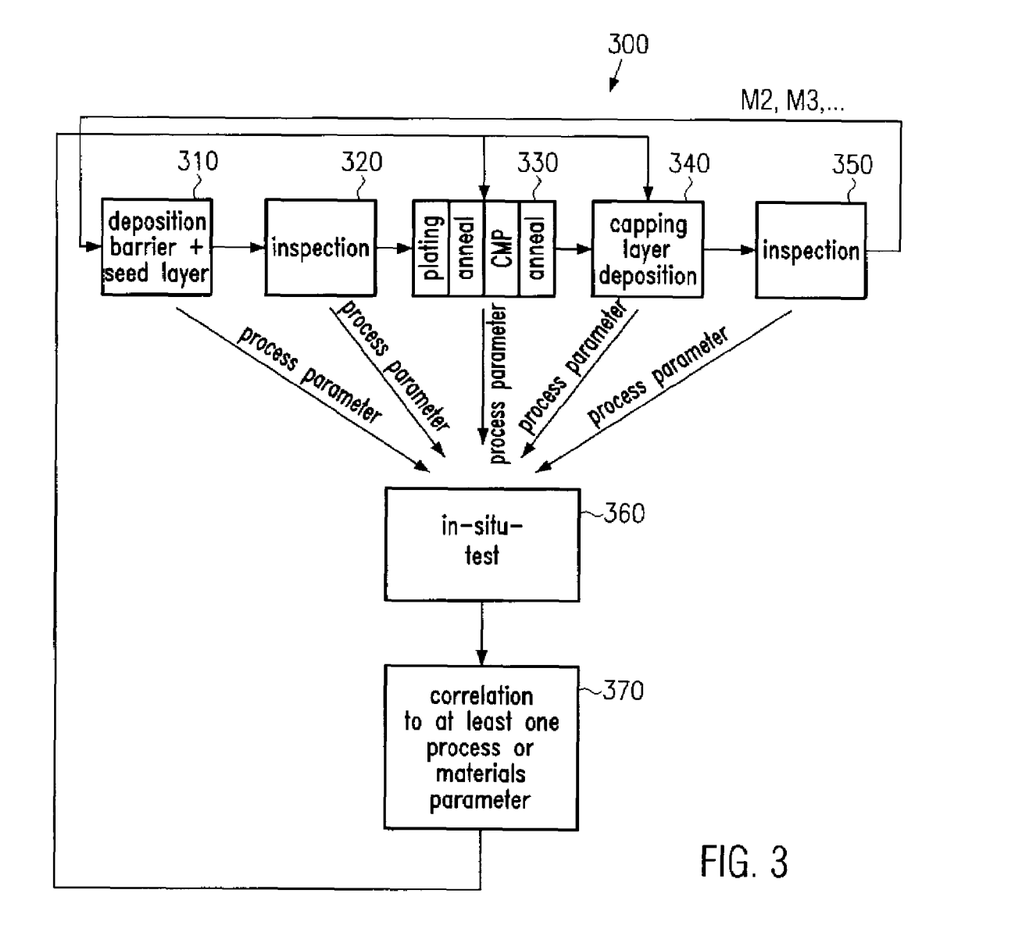
FIG. 3 schematically illustrates a specific manufacturing environment for forming a stacked metallization structure by controlling at least one process parameter on the basis of texture-specific information obtained from one or more metallization structures formed in the manufacturing environment.

FIG. 3 schematically represents a process sequence 300 for forming a metallization structure, as is for instance described with reference to FIG. 1a. Box 310 represents processes related to the formation of a conductive barrier layer and possibly a seed layer, wherein these processes may include chemical and physical vapor deposition, atomic layer deposition, electroless plating processes and the like. Box 320 represents any inspection processes performed after having formed the barrier layer. Box 330 represents the deposition process for the bulk metal, such as copper, on the basis of electroplating or electroless plating. Moreover, Box 330 is to represent any post-plating processes such as CMP, electropolishing and the like for removing any excess material. Moreover, anneal cycles performed prior to and/or after the CMP process may also be represented by Box 330, wherein highly advanced anneal techniques or other treatments for obtaining enlarged metal grains may be included, the efficiency of which may thus be effectively monitored and/or controlled on the basis of the x-ray measurement technique described above. Box 340 indicates the deposition of any type of capping layer, such as dielectric or conductive capping layers, followed by Box 350 representing inspection and other measurement procedures, such as measurement processes described with reference to FIGS. 1c-1f and 2, for evaluating the texture characteristics of the corresponding metal lines. Thereafter the sequence 300 may be repeated with appropriately adapted parameter values to form further metallization layers.

In the process steps 310, 320, 330, 340, 350, materials and process parameters may change in accordance with device and process requirements for the microstructure of interest since, for example, the grain size and orientation, which may be influenced by the process strategies and the materials used, may be essential for the proper operation of the metallization structure and may even become more important as feature sizes are steadily decreased. As previously explained, a complex mutual interaction of the materials and process parameters may significantly influence the finally obtained crystalline structure. Therefore, according to one illustrative embodiment, an in situ measurement which may also include a degradation test, represented by Box 360, may be performed similarly as is described with reference to FIGS. 1c-1f and 2, thereby enabling a sensitive monitoring of the involved materials and process parameters. For instance, a change of the geometry, i.e., the dimensions of the metal lines, may lead to subtle changes of the grain orientation and/or size, although substantially the same process parameters and materials may have been used in the manufacturing sequence 310, 320, 330, 340, 350 as in previously fabricated metallization structures exhibiting satisfactory results.

Based on the in situ test 360, a corresponding correlation between one or more materials or process parameters may be established with respect to their influence on the finally obtained crystallinity of the respective metal regions. Consequently, process flow failures may be readily identified on the basis of the respective measurement results. Moreover, the in situ test 360 enables efficient monitoring of process variations within the sequence 310, 320, 330, 340, 350 which may not have been identified within the individual processes. For instance, it may be assumed that, according to results provided by the inspection processes 320 and 350, or other additional metrology processes, the individual processes 310, 330 and 340 may lie within the respectively defined process margins, while nevertheless the finally obtained metallization structure may have a non-desired texture identified by the test 360. In other embodiments, a correlation may be established as indicated by 370 that relates at least one process parameter and/or material to the measurement results obtained by the test 360 so that a "long term" process control may be achieved. For instance, from previously performed reference measurements, an influence of, for example, process materials and parameters of the barrier/seed deposition process 310 may have been determined for a plurality of materials and process parameter values. Upon detection of a deviation of periodically performed tests 360, a corresponding re-adjustment of process parameters and/or materials may then be performed. Thereafter, one or more subsequent substrates may be processed on the basis of the re-adjusted parameters and/or materials. The same holds true for the further process steps 320, 350. For instance, measurement results of the inspection steps 320 and 350 may be effectively correlated with the results of the in situ test 360, thereby providing the capability for detecting relevant process fluctuations at an early stage in the sequence 300. For example, the measurement results with respect to the texture, that is, grain size and/or grain orientation, may be related to degradation mechanisms identified by the test 360, wherein, by means of the correlation 370 and corresponding routinely performed measurements, a process may be identified which may have otherwise been estimated as adequate. In this way, the "sensitivity" of one or more inspection processes involved in the sequence 300 may be enhanced with respect to the finally obtained reliability of metallization structures.

As a result, the present invention provides an enhanced technique for the inspection of texture and crystallinity of metal lines in a stacked metallization structure on the basis of x-ray techniques combined with data reduction in order to obtain measurement results for individual metallization layers in the metallization stack. For this purpose, appropriate "reference data" may be obtained to "reduce" the substantially three-dimensional data of the entire stack in an appropriate fashion to allow the extraction of information of one specific metallization level. Consequently, the advantages of x-ray analysis with respect to sample integrity as well as sample preparation compared to charged particle measurement techniques may be used while still providing the possibility of "resolving" the measurement results to individual metallization layers. Consequently, the influence of process parameters and materials on the crystalline structure of metal lines may be investigated more efficiently and furthermore the relation between electromigration or other stress-induced transport phenomena and the crystallinity of respective metal lines may be examined and may allow an efficient identification of degradation mechanisms and/or process control.

The particular embodiments disclosed above are illustrative only, as the invention may be modified and practiced in different but equivalent manners apparent to those skilled in the art having the benefit of the teachings herein. For example, the process steps set forth above may be performed in a different order. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed:

1. A method, comprising:
    irradiating a portion of a first stacked metallization structure of a microstructure device with an x-ray beam of specified characteristics, said first stacked metallization structure comprising a plurality of layers, each layer comprising a metal region;
    obtaining first measurement data of a plurality of said metal regions of said portion on the basis of said x-ray beam wherein said plurality of metal regions is located in two or more of said plurality of layers;
    manipulating said first measurement data to obtain manipulated data relating to a texture of one or more of said metal regions; and
    extracting information for at least one of said plurality of stacked layers about said texture on the basis of said manipulated data.

2. The method of claim 1, wherein manipulating said first measurement data comprises:
    irradiating a second stacked metallization structure of a microstructure with an x-ray beam having said specified characteristics to obtain second measurement data, said second metallization structure formed according to the same design rules as said first metallization structure and having a reduced number of layers compared to said first metallization structure; and
    relating said first measurement data to said second measurement data to obtain said manipulated data.

3. The method of claim 2, wherein said first stacked metallization structure comprises n layers and said second stacked metallization layer comprises n-1 layers and wherein a last layer of said second stacked metallization structure corresponds to a penultimate layer of the first stacked metallization structure.

4. The method of claim 2, wherein obtaining said manipulated data comprises subtracting a first data correlated to said first measurement data from a second data correlated to said second measurement data to obtain differential data and using the same for obtaining said manipulated data.

5. The method of claim 4, wherein obtaining said manipulated data further comprises applying at least one correction algorithm to said differential data and using said corrected differential data as said manipulated data.

6. The method of claim 1, wherein extracting said information about a texture of at least one of said plurality of layers comprises evaluating at least one of a grain size and an orientation of grains formed in each of said metal regions.

7. The method of claim 1, wherein irradiating said first stacked metallization structure to said x-ray beam of specified characteristics comprises forming a substantially mono-energetic x-ray beam and varying an angle of incident of said x-ray beam.

8. The method of claim 7, further comprising detecting an intensity of an x-ray beam reflected from said portion for a plurality of different angles of incidence.

9. The method of claim 1, wherein irradiating said first stacked metallization structure to said x-ray beam of specified characteristics comprises forming an x-ray beam having a plurality of different wavelengths and directing said x-ray beam onto said portion under a specified angle of incidence.

10. The method of claim 9, further comprising detecting an intensity of an x-ray beam reflected from said portion for a plurality of different detection angles.

11. The method of claim 10, further comprising establishing specified stress conditions for said first stacked metallization structure and obtaining, as said first measurement data, a plurality of data sets corresponding to said specified stress conditions.

12. The method of claim 11, wherein said specified stress conditions comprise a condition to cause electromigration effects to occur in said metallization structure.

13. The method of claim 11, further comprising visualizing said extracted information while said specified stress conditions are applied to obtain a time progression of a variation of said texture.

14. A method, comprising:
forming a stacked metallization structure of a microstructure device according to a specified manufacturing sequence, said stacked metallization structure comprising a plurality of metallization layers;
obtaining information about a texture of metal regions located in two or more of said plurality of metallization layers on the basis of x-ray analysis;
correlating at least one process parameter used in said specified manufacturing sequence with said texture information; and
controlling said at least one process parameter on the basis of said correlation.

15. The method of claim 14, wherein said information relates to at least one of a size and an orientation of grains formed in said metal regions.

16. The method of claim 15, wherein said texture information is obtained for each of said plurality of metallization layers.

17. The method of claim 14, wherein said metallization structure comprises copper and a low-k dielectric material.

18. The method of claim 14, wherein obtaining said information comprises obtaining first measurement data from a first metallization layer, obtaining second measurement data from a second metallization layer, obtaining differential data from said first and second measurement data and extracting said information on the basis of said differential data.

19. The method of claim 14, further comprising determining a relationship between said information and at least one stress-induced degradation process and controlling said specified manufacturing sequence on the basis of said relationship.

20. A method, comprising:
providing a metallization structure of a microstructure device, said metallization structure comprising a plurality of stacked metallization layers, each metallization layer comprising a metal region with metal grains;
subjecting said metallization structure to predefined stress conditions; and
estimating a distribution of grain orientations in at least one of said plurality of stacked metallization layers by x-ray analysis that covers two or more of said plurality of stacked metallization layers under said predefined stress conditions.

21. The method of claim 20, wherein estimating a distribution of grain orientations comprises:
obtaining first x-ray measurement data from said metallization structure;
obtaining second x-ray measurement data from a reference metallization structure including a lower number of stacked metallization layers compared to said metallization structure; and
obtaining differential data on the basis of said first measurement data and said second measurement data to estimate said distribution based on said differential data.

* * * * *